United States Patent
Holmertz et al.

(10) Patent No.: US 7,681,523 B2
(45) Date of Patent: Mar. 23, 2010

(54) METHOD AND APPARATUS FOR COUNTING SOMATIC CELLS OR FAT DROPLETS IN MILK

(75) Inventors: Nils Erik Holmertz, Huddinge (SE); Epke Bosma, Tumba (SE)

(73) Assignee: DeLaval Holding AB, Tumba (SE)

( * ) Notice: Subject to any disclaimer, the term of this patent is extended or adjusted under 35 U.S.C. 154(b) by 196 days.

(21) Appl. No.: 10/540,478

(22) PCT Filed: Feb. 17, 2004

(86) PCT No.: PCT/SE2004/000204

§ 371 (c)(1), (2), (4) Date: Jun. 23, 2005

(87) PCT Pub. No.: WO2004/073391

PCT Pub. Date: Sep. 2, 2004

(65) Prior Publication Data

US 2006/0249082 A1  Nov. 9, 2006

(30) Foreign Application Priority Data

Feb. 18, 2003 (SE) .................................. 0300431

(51) Int. Cl.
*A01J 5/13* (2006.01)
(52) U.S. Cl. .................................................. 119/14.02
(58) Field of Classification Search ............... 119/14.01, 119/14.02, 14.08, 14.1, 14.14, 14.17, 14.18; 324/71.4; 356/336; 382/133
See application file for complete search history.

(56) References Cited

U.S. PATENT DOCUMENTS

| 3,762,371 | A | 10/1973 | Quayle et al. |
| 5,302,903 | A | 4/1994 | De Jong et al. |
| 5,416,417 | A | 5/1995 | Peles |
| 5,594,544 | A | 1/1997 | Horiuchi et al. |

(Continued)

FOREIGN PATENT DOCUMENTS

EP    1000535 A1    5/2000

(Continued)

OTHER PUBLICATIONS

"Influence of different milking intervals on electrical conductivity before alveolar milk ejection in cows", K. Barth and H. Worstorff, Milchwissenschaft 55(7), 2000, p. 363.

(Continued)

*Primary Examiner*—T. Nguyen
(74) *Attorney, Agent, or Firm*—Harness, Dickey & Pierce, PLC (57) ABSTRACT

A method for counting somatic cells or fat droplets in milk on-line during milking by an automated or semi-automated milking system comprising the steps of: flowing milk as milked by the milking system through a measuring chamber (59); illuminating milk that flows through the measuring chamber; and recording multiple two-dimensional digital images of illuminated milk that flows through the measuring chamber, wherein the images are recorded through a lens system (49) to preferably obtain a spatial resolution better than about 5 microns in the images. Finally, a somatic cell or fat droplet count score of the milk is determined from the images by means of digital image processing, preferably including the use of neural networks.

37 Claims, 5 Drawing Sheets

U.S. PATENT DOCUMENTS

| | | | |
|---|---|---|---|
| 6,104,483 A | 8/2000 | Sebok et al. | |
| 6,297,045 B1 | 10/2001 | Takahashi et al. | |
| 6,297,505 B1 | 10/2001 | Frandsen et al. | |
| 6,307,362 B1 | 10/2001 | Mangan | |
| 6,367,416 B1 * | 4/2002 | van der Lely et al. | 119/14.02 |
| 6,378,455 B1 | 4/2002 | Postma et al. | |
| 6,694,830 B2 * | 2/2004 | Hakes | 73/863.53 |
| 6,731,100 B1 * | 5/2004 | Hansen et al. | 324/71.4 |

FOREIGN PATENT DOCUMENTS

| | | | |
|---|---|---|---|
| EP | 1180675 A2 | 2/2002 | |
| GB | 2 152 660 | 8/1985 | |
| WO | WO 0027183 A1 | 5/2000 | |

OTHER PUBLICATIONS

International Search Report.

PCT International Preliminary Report on Patentability dated Aug. 19, 2005 for PCT/SE2004/000204, including Written Opinion of the International Searching Authority.

* cited by examiner

METHOD AND APPARATUS FOR COUNTING SOMATIC CELLS OR FAT DROPLETS IN MILK

TECHNICAL FIELD OF THE INVENTION

The present invention relates generally to dairy farming, and more specifically to methods and apparatuses for counting somatic cells or fat droplets in milk.

DESCRIPTION OF RELATED ART AND BACKGROUND OF THE INVENTION

A major cause of loss in dairy farming is an infection, known as mastitis, which occurs in an animal's udder. Mastitis is caused by contagious pathogens invading the udder and producing toxins that are harmful to the mammary glands. Generally, mastitis starts in one udder quarter.

Somatic cells, predominantly white cells and epithelial cells, enter the mammary gland as a result of damage to the alveolar lining by infection or chemical irritation. The counting of somatic cells excreted in the milk has become a widely used measure of mammary gland inflammation. The somatic cells can be counted by laborious direct microscopic method on stained milk smears, or the cell numbers can also be estimated by direct chemical tests. Other methods measure milk somatic cells indirectly or by determining the concentration of various by-products of the inflammatory response.

Somatic cell count (SCC), which is the number of white cells per milliliter of milk, increases in the bulk tank as mastitis spreads in the herd. SCC scores are used as an international standard in determining milk's quality and price. Most marketing organizations and regional authorities regularly measure SCC on bulk tank milk and use these scores for penalty deductions and/or incentive payments. High SCC scores indicate the presence of mastitis in the herd, which is reflected in the average score of the bulk tank. The bulk tank SCC is a good indicator of overall udder health and as good means for evaluating the mastitis control program.

It is also a high correlation between the bulk milk SCC and the average of individual animal counts. It is not uncommon for a few problem animals to be responsible for greater than 50% of the somatic cells in the bulk tank, particularly in small herds. It should be noted that animals with high milk production and intermediate SCC levels can have a significantly higher percentage of SCC contribution to the tank score than some high SCC cows with low production. For high quality milk the SCC should be less than 200,000 cells/ml. Acceptable milk has SCC scores from 200,000 to 500,000 cells/ml. For infected animals, milk SCC scores are between 600,000 and 1.2 million cells/ml.

When an animal in the herd becomes infected with infectious pathogens a rapid drop in milk production will be noted within two to three days. A high level of bacteria in an animal causes an increased level of somatic cells in milk. An increased level of somatic cells in milk results in poorer quality milk products, which are harder to process. The prevention procedures at milking are less efficient especially when the mastitis is in a subclinical phase and there are no visible signs of the disease. Special efforts have to be made at each milking to detect subclinical mastitis in individual animals.

SCC may be measured by CMT (California Mastitis Test) by utilizing the difference in the extent of aggregation reaction depending on the number of somatic cells, when a surfactant is added to the milk. Since a BTB reagent is also included for pH measurement, it is used as an evaluation index for mastitis by utilizing the fact that increased vascular permeability and accelerated conflict between leukocytes and bacteria during mastitis results in increased salts such as sodium chloride and potassium chloride in the milk, creating a higher alkalinity, and causing a color change from yellow to green and then to blue. The advantages of this measurement are that it can be easily performed by anyone, it can generally distinguish between the presence and absence of mastitis, and it is an extremely low-cost method. The drawbacks of CMT are that diagnosis is difficult until the reaction has occurred, involving the conflict between leukocytes and the bacteria, or after promotion of vascular permeability, and that diagnosis depends on subjective human judgment, so that this method can only serve as an approximate diagnosis method. Diagnosis has been particularly rough in cases where the milk somatic cell count is 300,000/ml or less. The method is thus not suitable to be automated.

Measuring CL (chemiluminescence) activity has also been used for determining the SCC, see e.g. U.S. Pat. No. 6,297,045. A related method is to add to the milk a fluorescent additive, which is absorbed by the cells. By illuminating the milk with light of a particular wavelength the cells will emit a fluorescent light of another characteristic wavelength. By a suitable filter, which filters out light of the characteristic wavelength, the number of cells can be counted.

Such an approach requires that milk samples are taken, that a suitable amount of fluorescent additive has to be added and mixed with the milk, and that particular light sources and filters are used. This is a labor intense and costly procedure. If the method is automated in a milking robot system, particular provisions have to be taken in order to obtain and separate small amounts of milk, which is representative of the milk from a cow or an udder of a cow.

Mastitis may alternatively be detected by measuring changes in the electrical conductivity of milk as generally, ion concentration, and thus electrical conductivity, in mastitic milk is higher than in normal milk. Electrical conductivity is generally measured with a DC or AC circuit having a probe positioned in the flow of milk. The most sensitive part of this on-line method is the probe. The probe generally includes two electrodes to which an AC or DC current is supplied to create an electrical circuit through the milk. The conductivity of the milk is evaluated by measuring the current variations in the circuitry that includes the probe. However, the readings are often inaccurate due to deposits of colloidal materials from the milk on the electrodes, and also due to polarization. Polarization occurs because some of the ions migrating towards the electrodes are not neutralized and consequently, an offset, or leakage current is generated between the electrodes. The presence of the leakage current results in inaccurate conductivity readings. Different aspects on milk conductivity measurements have been patented, see e.g. U.S. Pat. Nos. 3,762,371; 5,416,417; 5,302,903; 6,307,362 B1; and 6,378,455 B1.

Conductometry has disadvantages in that it depends on changes occurring by inflammation reaction after the bacteria invade and conflict with the leukocytes, and therefore it is unsuitable for diagnosis in the initial stages of mastitis, while it has poor reproducibility due to substantial differences in electrolyte components and concentrations in different teats or different cows even with normal milk, such that diagnosis is risky by this diagnostic method alone.

Another potential problem using milk conductivity measurements to discover mastitis is that the conductivity of the milk is heavily dependent on the milking intervals, see *Influence of different milking intervals on electrical conductivity before alveolar milk ejection in cows*, K. Barth and H. Worstorff, Milchwissenschaft 55(7), 2000, p. 363. Thus, the milking intervals have to be taken into consideration if milking times are not as fixed as in conventional milking systems.

SUMMARY OF THE INVENTION

A general object of the present invention is to provide a method and an apparatus, respectively, for counting somatic cells or fat droplets in milk on-line during milking by an automated milking system, which lack the drawbacks and limitations associated with the prior art described above.

A particular object of the invention is to provide such a method and such an apparatus, which are completely automatic and provide a reliable somatic cell or fat droplet count score.

It is a further object of the invention to provide such a method and such an apparatus, which count somatic cells or fat droplets directly in a milk line of the automated milking system.

It is yet a further object of the invention to provide such a method and such an apparatus, which are capable of providing a separate somatic cell count or fat droplet score for each udder quarter of a cow.

It is still a further object of the invention to provide such a method and such an apparatus, which are reliable, flexible, of fairly low cost, and relatively easy to implement.

These objects, among others, are according to the present invention attained by methods and apparatuses as specified in the appended patent claims.

Further characteristics of the invention, and advantages thereof, will be evident from the following detailed description of preferred embodiments of the present invention given hereinafter and the accompanying FIGS. 1-6, which are given by way of illustration only, and thus are not limitative of the present invention.

DETAILED DESCRIPTION OF EMBODIMENTS

Figure 1:
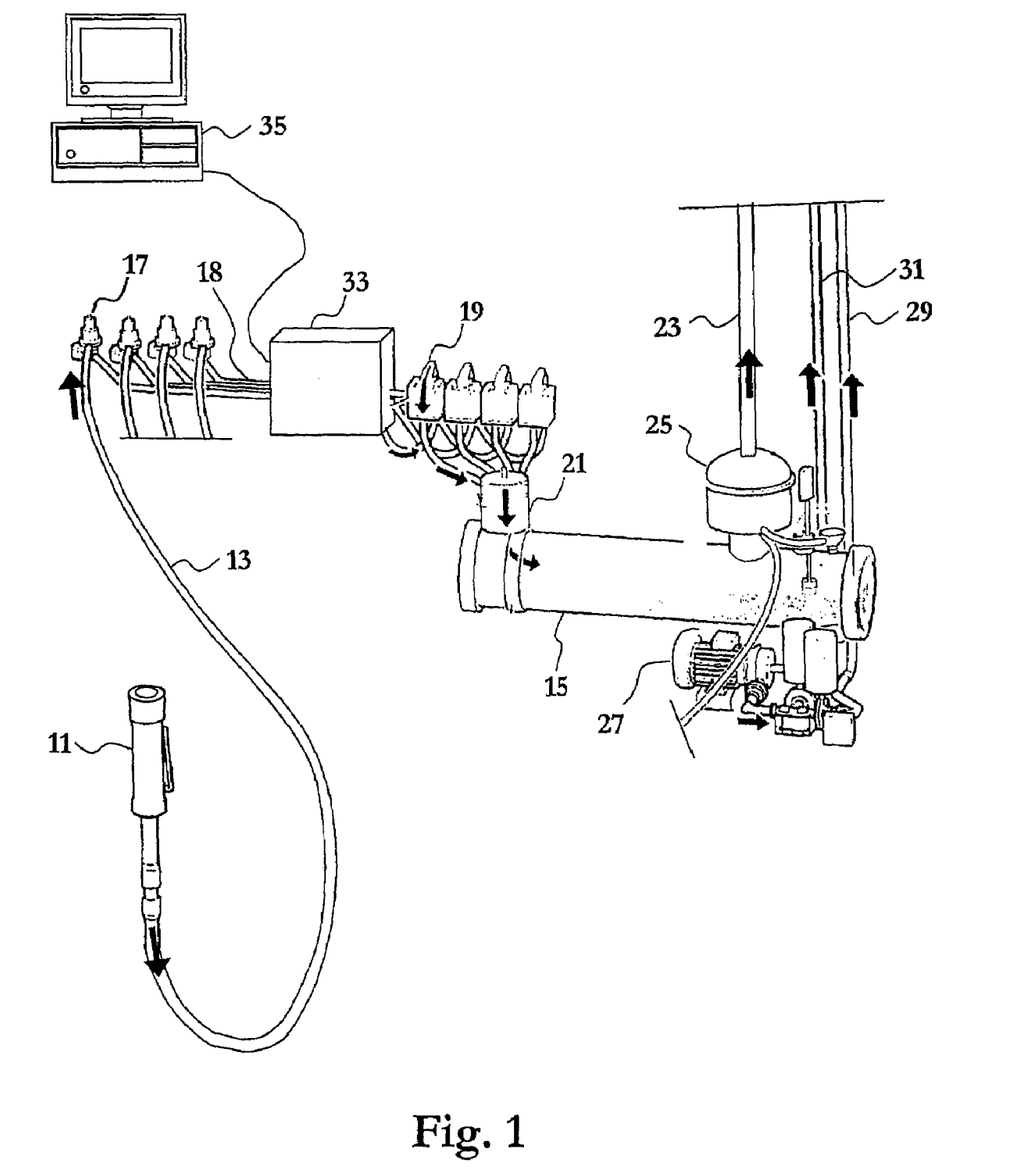
FIG. 1 illustrates schematically, in a perspective view, main components of a milking robot provided with an apparatus for counting somatic cells or fat droplets in milk on-line during milking according to a general embodiment of the present invention.

FIG. 1 illustrates some of the main components of a milking robot. The milking robot comprises four teat cups 11, of which only one is illustrated for sake of simplicity. Each teat cup 11 is connected to a respective milk tube 13, which in turn is connected to an end unit 15 via a respective valve or regulator 17, a respective milk conduit 18, a respective flow meter 19, and a common milk meter 21. The end unit is connected to a vacuum source (not illustrated) via a milk/air separator and a vacuum supply conduit 23.

During milking of the teats of a milking animal, the teat cups are attached to the teats of a cow, typically by a robot arm (not illustrated), and vacuum is supplied to the end unit 15 via the vacuum supply conduit 23 to draw milk from the teats of the cow, through the milk lines 13 and into the end unit 15. The valves or regulators 17 may be used to control the individual vacuum levels in the teat cups 11. The milk from each udder quarter of the cow is measured individually by the flow meters 19, whereafter the weight of the milk from the cow is measured by the common milk meter 21. Finally, the milk is collected in the end unit 15 and the air is sucked out through the conduit 23.

Further, the milking robot comprises a pump and regulator system 27 for pumping the milk to e.g. a larger milk storage tank (not illustrated) via one 29 of a plurality of milk output lines 29, 31 connected to the end unit 15. Another milk output line 31 may be used for discarding milk from the milking of a cow, for pumping the milk to another tank (not illustrated), or for pumping the milk to a feed device for feeding calves.

The milking robot is advantageously connected to a computer-based processing and control device 35, which is responsible for processing and controlling of the milking robot, and comprises typically a microcomputer, suitable software, and a database including information of each of the cows milked by the milking robot, such as e.g. when the respective cow was milked last time, when she was fed last time, her milk production, her health, etc.

For the purpose of identifying cows, which have an increased SCC scores, e.g. in order to treat or monitor these cows, or in order to direct the milk from them to not mix it with milk from healthy cows or cows having low SCC scores, the present invention presents an improved technique for counting somatic cells in milk on-line during milking.

An inventive apparatus for counting somatic cells or fat droplets in milk on-line during milking, schematically shown by reference numeral 33 in FIG. 1, comprises generally a flat or shallow measuring chamber, a light source, a two-dimensional camera system including a lens system, preferably a microscope, and a digital image processing system. A particular embodiment of the apparatus is illustrated in detail in FIGS. 2-3, which embodiment will be described further below.

The flat measuring chamber is arranged so that at least a portion of the milk drawn from the teats of a cow, through the milk lines 13, and into the end unit 15 is flowed though the measuring chamber. The light source is set to illuminate milk that flows through the flat measuring chamber, and the two-dimensional camera system is adapted to repeatedly record two-dimensional digital images of the illuminated milk that flows through the flat measuring chamber. The camera array and the lens system are adapted so that a rather small image area is recorded, but with high magnification. A spatial resolution better than about 5 microns in the two-dimensional digital images is preferred. Finally, the digital image processing system is adapted to determine, e.g. by use of neural networks, a somatic cell or fat droplet count score from the two-dimensional images.

Preferably, the digital image processing system is implemented in the processing and control device 35.

The flat measuring chamber may be arranged in a separate conduit, provided for leading away a portion of the milk from one or several of the milk conduits 18. Optionally, the milk is brought back to the milk conduit(s) 18 or is brought to the end unit 15 after having passed the flat measuring chamber. Advantageously, however, the flat measuring chamber is arranged within one of the milk conduits 18.

Figure 2:
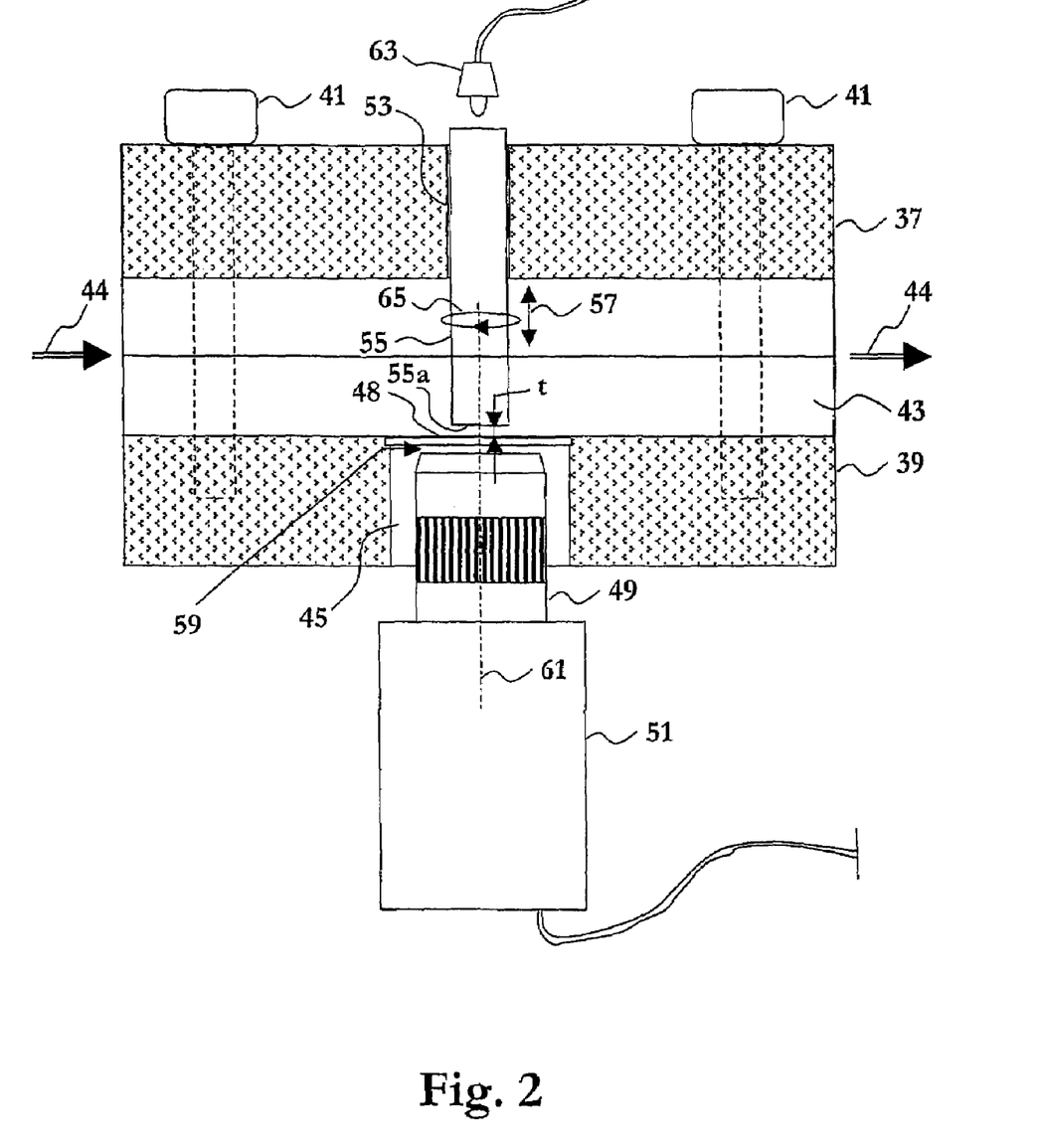
FIGS. 2-3 illustrates schematically, in cross-sectional top and end views, an apparatus for counting somatic cells or fat droplets in milk on-line according to a particular embodiment of the present invention.
Figure 3:
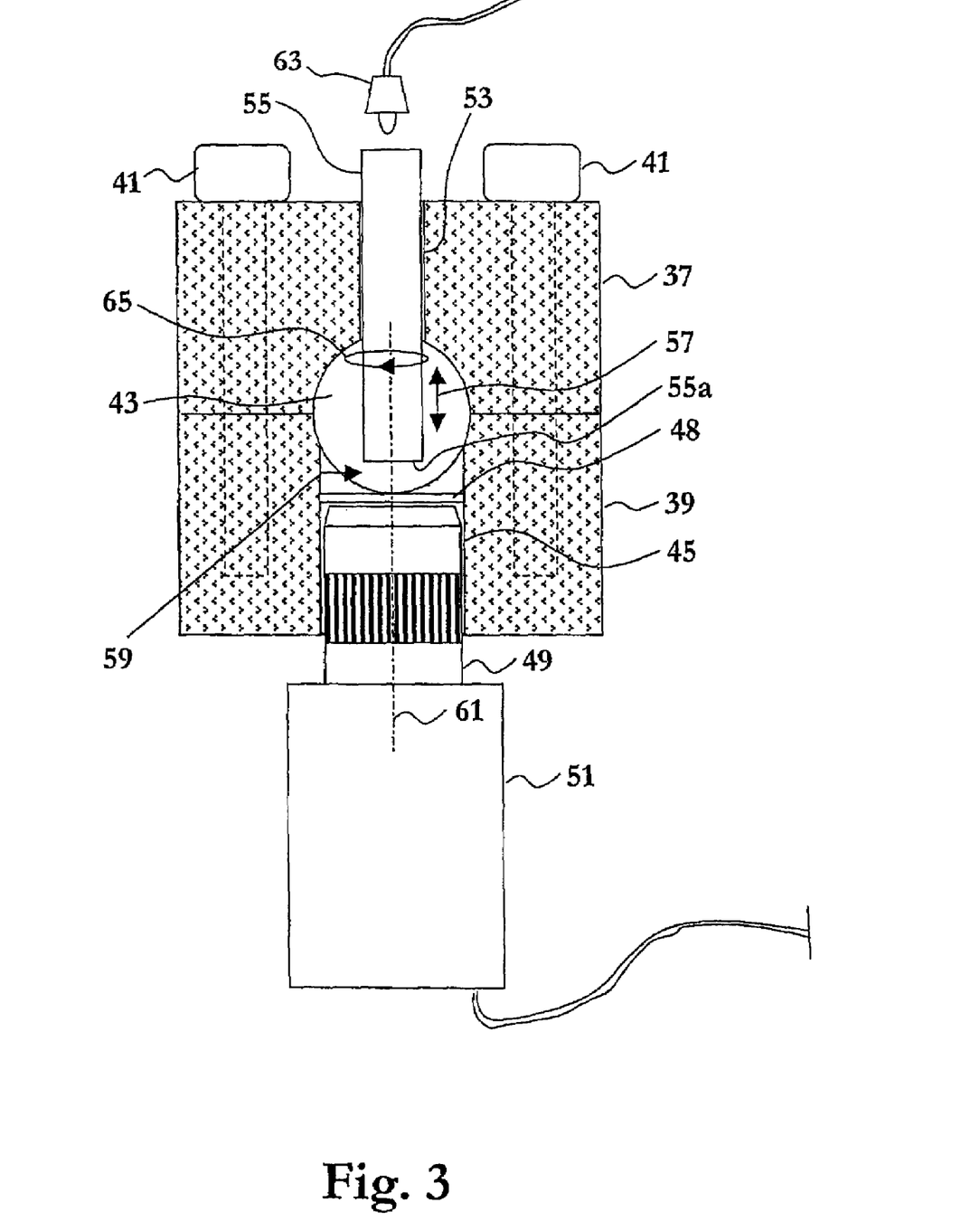

Such solution is adopted by the particular embodiment of the apparatus as being illustrated in FIGS. 2-3. A measuring cell comprises a top and a bottom cell block 37, 39, which when being attached to each other in a fluid tight manner by means of four bolts 41 or similar form a milk passageway 43 from left to right. The passageway 43 has preferably a circular cross section as illustrated. The measuring cell is mounted in one of the milk conduits 18 so that milk flows through the passageway 43 as indicated by arrows 44. Alternatively the cell blocks 37, 39 are designed to form a milk passageway of other cross sectional shape, e.g. quadratic or rectangular.

Further, the bottom cell block 39 of the measuring cell is provided with a substantially vertical through hole 45. The surface of the bottom cell block 39, which together with a corresponding surface of the top cell block 37, form the passageway 43, is shaped to be plane within a major portion of a given area. A light transparent plate 48 fitted within the flat portion is glued to the bottom cell block 39 in a fluid tight manner. The position of the plane surface portion of the bottom cell block 39 is selected so that the upper surface of the plate 48 is in level with the lowest portion of the surface forming the passageway 43 outside the area. The passageway surface of the bottom cell block 39 within the given area, but outside the plane surface portion, may be shaped to obtain a smooth transition to the passageway surface of the bottom cell block 39 outside the given area. By providing smooth surfaces within the measuring cell, pockets where milk may be accumulated are avoided. The size of the hole 45 is selected such that the front portion of a two-dimensional camera system 51, e.g. CCD-based system, provided with a lens system 49, preferably a microscope, for magnification can be inserted into the hole 45 as illustrated.

The top cell block 37 of the measuring cell is provided with a substantially vertical through hole 53, preferably smaller than the hole 45, and aligned with the hole 45. A rod 55 is fitted to be inserted to the through hole 53 so that a flat end surface 55a of the rod 55 is located in the passageway 43 opposite to and parallel with the plate 48. The rod 55 is tightly fitted in the through hole 53 to prevent milk from leaking out through the hole 53, and is movable in a vertical direction as is indicated by arrow 57.

The flat measuring chamber 59 is defined as the space between the plate 48 and the flat end surface 55a of the rod 55. Thus, the flat measuring chamber 59 is open in directions being parallel with the plate 48 and the surface 55a, and orthogonal to a general direction of the flow of milk as indicated by the arrows 44. During SCC measurements the thickness t of the measuring chamber 59, i.e. the dimension of the measuring chamber 59 in a direction parallel with the optical axis 61 of the camera system 51 during measurements, is preferably smaller than about 100 microns, more preferably smaller than about 50 microns, and most preferably smaller than about 10 microns. It is important to obtain a depth of field and focusing of the camera system 51 so that the images are sharp; and to reduce the probability of cells "hiding" behind an imaged cell. Such cells will obviously not be counted.

The rod 55 is preferably light transparent to allow for illumination of the milk that flows through the flat measuring chamber 59 by a light source, schematically indicated by 63, through the rod 55. It shall, however be appreciated by the man skilled in the art that other illumination techniques may be used including i.a. mirror and beamsplitter arrangements. Milk in the flat measuring chamber 59 may be illuminated from above as illustrated or from below, i.e. from the camera system 51 side. In the latter instance the end surface 55a of the rod 55 may be light reflecting.

In general, light as transmitted trough milk in the measuring chamber is recorded by the camera system. Alternatively or additionally, light as reflected by milk in the measuring chamber is recorded. Further, the orientation of the measuring chamber 59 and the camera system 51 may different from what is illustrated in FIGS. 2-3.

The milk is sucked through the lines 18 intermittently and is mixed with air. Thus, it is particularly advantageous to have the measuring chamber 59 arranged at the very bottom of the passageway 43 as it is most probable that milk will pass through there due to gravity. In order to assure that milk is not clogged in the measuring chamber 59, the rod may be rotated around the axis 61 continuously during measurements as being indicated by arrow 65. The rod may be moved vertically and be rotated automatically by means of a motor (not illustrated) connected to the processing and control device 35.

The camera system 51 is preferably provided with a microscope or tele/macro photo lens system 49 to record strongly magnified two-dimensional images. Preferably, the camera system 51 provides for a spatial resolution in the two-dimensional digital images better than 2 microns, more preferably better than about 1 micron, and most preferably better than about 0.5 microns. As a result thereof very small areas are recorded and probably a very large number of images have to be recorded in order to provide accurate and precise SCC scores.

Figure 4:
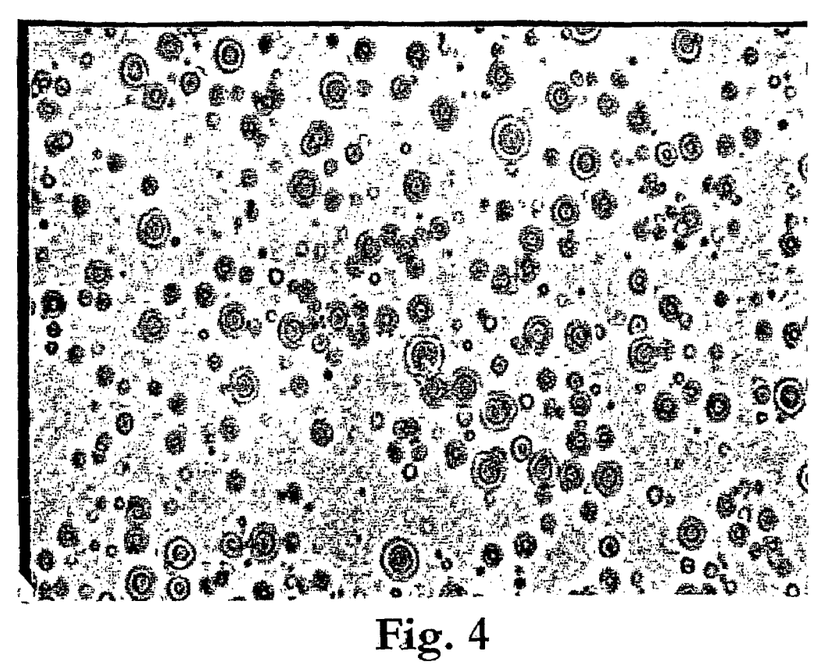
FIGS. 4-6 show three examples of two-dimensional digital images as recorded by the apparatus of FIGS. 2-3 during counting of somatic cells or fat droplets.
Figure 5:
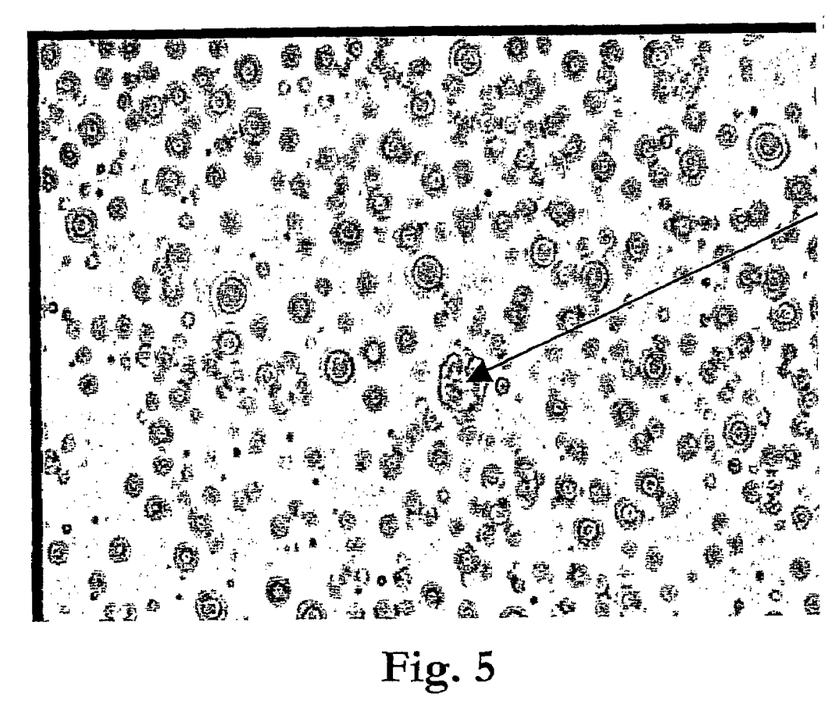
Figure 6:
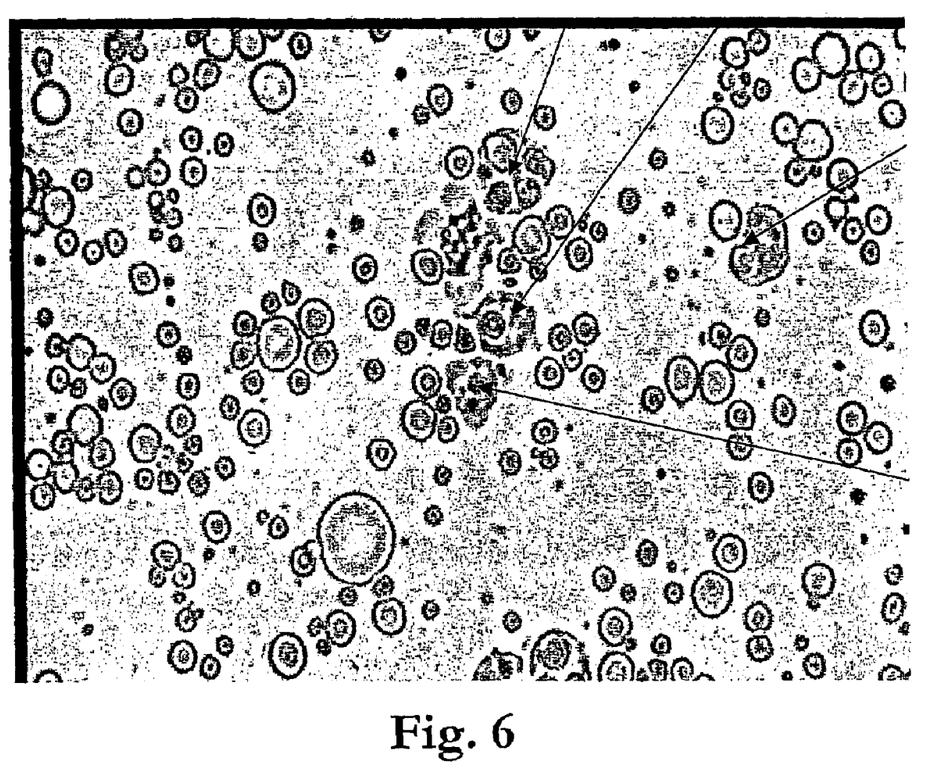

Three different two-dimensional images as recorded by a SCC measuring apparatus according to the principles of the present invention, but set up in a laboratory environment, are illustrated in FIGS. 4-6.

In the first image (FIG. 4) only fat droplets are visible, whereas in the second and third images (FIGS. 5-6) several somatic cells are identified among a large number of fat droplets (the somatic cells are indicated by the arrows). As can be seen in FIGS. 5-6 the somatic cells look quite different than the fat droplets and these differences are used by the digital image processing system to distinguish the different particles in the images. Generally, the digital image processing employed includes the analysis of number, size, shape, structure, morphological structure, density and/or composition of particles found in each image as revealed by the reflection and/or transmission properties of the particles as found in the images recorded. Preferably, the image processing system uses neural networks.

Using a 600×400 pixel CCD-camera provided with a microscope to record images covering an area of 0.3×0.2 mm$^2$ the spatial resolution in the images is estimated to be about 0.5 microns. Using a measuring chamber with a thickness of about 0.1 mm each sample volume imaged amounts to 0.6×10$^{-6}$ ml. Thus given a SCC score of 1 million cells/ml, which may be a typical score for an infected cow an average of only 0.6 cells/image will be found in each image. By recording a large number, e.g. thousands, of images, and by means of digital image processing of these images a somatic cell count score can be determined.

The somatic cells are in some instances, e.g. when the milk is mastitic, predominantly white cells, and thus the somatic cell count score may be a count score of white cells. In other instances, e.g. for healthy animals having naturally high SCC scores, the number of epithelial cells are higher. In still other instances, e.g. in case of serious disease or injury, the number of red blood cells may be estimated.

From number and size of fat droplets in the images a content of fat may also be estimated using digital imaging processing.

While the particular embodiment of the SCC measuring apparatus has been described as being mounted in one of the milk conduits 18, and thus measures SCC in a single udder quarter, it may be connected downstream of the point where milk from the udder quarters are mixed. For instance in a milking machine where the teat cups are connected to a single milk line via a claw (upstream of the end unit), the SCC measuring apparatus may be located in this single milk line. However, since mastitis often starts in one or maybe two udder quarters, this is not the most preferred solution as the detection sensitivity for mastitis is reduced when milk from infected udder quarters are mixed with milk from healthy udder quarters before the SCC measurement takes place.

The most flexible solution is to have a measuring cell mounted in each one of the milk lines 18 in the robot of FIG. 1, and then to provide one light source and one camera system for each measuring cell, or to provide a single light source or camera system which is alternately used for SCC measurement of milk that is flowed through the various measuring cells. Then, the SCC scores for the different udder quarters may be compared to obtain a very sensitive detection of mastitis or increased SCC scores in milk from individual udder quarters.

It shall further be appreciated, that by implementing the above-identified flexible solution, a milking robot with four end units—one for each udder quarter, milk could be transported and taken care of on an udder quarter individual basis, e.g. milk from udder quarters having low SCC score is collected in one tank and milk from udder quarters having high SCC score is collected in an other tank.

It shall still further be appreciated by the person skilled in the art that the present invention may be implemented in virtually any kind of automated or semi-automated milking system.

The invention claimed is:

1. A method for counting cells or fat droplets in milk on-line during milking of a milking animal, wherein the steps of:
    flowing at least a portion of the milk as obtained during said milking of said milking animal through a measuring chamber;
    illuminating milk that flows through said measuring chamber;
    repeatedly recording about 1000 or more two-dimensional digital images of illuminated milk that flows through said measuring chamber, said two-dimensional digital images being recorded through a magnification lens system; and
    determining a somatic cell or fat droplet count score from said about 1000 or more two-dimensional images by means of digital image processing.

2. The method of claim 1 wherein said at least portion of the milk flowed through said measuring chamber is free from toxic additives.

3. The method of claim 1 wherein said at least portion of the milk flowed through said measuring chamber is pure natural milk, optionally mixed with air, but free from any chemical additives.

4. The method of claim 1 wherein said repeatedly recordings of two-dimensional digital images are performed to obtain a spatial resolution better than about 5 microns, in said two-dimensional digital images.

5. The method of claim 1 wherein said measuring chamber has a dimension (t) smaller than about 100 microns, in a direction parallel with the optical axis of said lens system during said repeated recordings.

6. The method of claim 1 wherein said digital image processing includes the analysis of number, shape, size, structure, density and/or composition of particles found in each image as revealed by at least one of the reflection and transmission properties of the particles recorded spatially resolved by said camera system.

7. The method of claim 1 wherein said digital image processing includes the use of neural networks.

8. The method of claim 1 wherein said at least portion of said milk, which is flowed through said measuring chamber, is lead away from a milk line of a milking machine used to collect the milk as obtained during said milking of said milking animal.

9. The method of claim 8 wherein said at least portion of said milk, which is lead away from said milk line, is brought back to said milk line or brought to a milk collecting container, after having been flowed through said measuring chamber.

10. The method of claim 1 wherein said at least portion of said milk is flowed through said measuring chamber within a milk line of a milking machine used to collect the milk as obtained during said milking of said milking animal.

11. The method of claim 1 wherein said milking of said milking animal is performed by an automated or semi-automated milking system, which comprises a plurality of teat cups, each of which being connected to a respective milk line, which milk lines in turn are connected to a container via a claw and a single milk line, wherein, during milking of the teats of said milking animal, said plurality of teat cups are attached to the teats of the milking animal and vacuum is supplied to said container to draw milk through said milk lines, said claw, said single milk line and into said container.

12. The method of claim 1 wherein said milking of said milking animal is performed by an automated or semi-automated milking system, which comprises a plurality of teat cups, each of which being connected to a respective milk line, which milk lines in turn are connected to a container wherein, during milking of the teats of said milking animal, said plurality of teat cups are attached to the teats of the milking animal and vacuum is supplied to said container to draw milk through said milk lines and into said container, wherein said milk is drawn in separate milk lines all the way to said container.

13. The method of claim 1 wherein said somatic cell or fat droplet count score is a count score of white cells.

14. The method of claim 11 wherein said container is provided with a plurality of milk output lines; and said milk drawn through the milk lines and into said container is output through one of said plurality of milk output lines depending on said somatic cell or fat droplet count score.

15. The method of claim 1 wherein a content of fat is estimated from said two-dimensional images by means of said digital imaging processing.

16. The method of claim 15 wherein said content of fat is estimated from number and size of fat droplets in said two-dimensional images.

17. The method of claim 12 wherein
    a measuring chamber is provided in each milk line;
    at least a portion of the milk drawn through the respective milk lines is passed through the respective measuring chambers;
    milk that flows through the respective measuring chambers is illuminated;
    two-dimensional digital images of illuminated milk that flows through the respective measuring chambers is repeatedly recorded, where said two-dimensional digital images are recorded through a lens system to obtain a spatial resolution better than about 5 microns in said two-dimensional digital images; and
    somatic cell or fat droplet count scores for milk drawn through the respective milk lines are determined from said two-dimensional images by means of digital image processing.

18. An apparatus for counting somatic cells or fat droplets in milk on-line during milking of a milking animal, wherein
    a measuring chamber, through which the milk as obtained during said milking of said milking animal is flowed;
    a light source system for illuminating milk that flows through said measuring chamber;
    a two-dimensional camera system including a lens system, for repeatedly recording about 1000 or more two-dimensional digital images of illuminated milk that flows through said measuring chamber, where said two-dimensional digital images are recorded through said lens system;

said lens system being a magnification lens system;

a digital image processing system for determining a somatic cell or fat droplet count score from said about 1000 or more two-dimensional images.

19. The apparatus of claim 18 wherein said at least portion of the milk flowed through said measuring chamber is free from toxic additives.

20. The apparatus of claim 18 wherein said at least portion of the milk flowed through said measuring chamber is pure milk natural milk, optionally mixed with air, but free from any chemical additives.

21. The apparatus of claim 18 wherein said two-dimensional camera system provides for a spatial resolution in said two-dimensional digital images better than about 5 microns, preferably better than about 2 microns, more preferably better than about 1 micron, and most preferably better than about 0.5 microns.

22. The apparatus of claim 18 wherein said measuring chamber has a dimension (t) smaller than about 100 microns, preferably smaller than about 50 microns, and more preferably smaller than about 10 microns, in a direction parallel with the optical axis of said lens system during said repeated recordings.

23. The apparatus of claim 18 wherein said digital image processing system is adapted to analyze number, shape, size, structure, density and/or composition of particles found in each image as revealed by reflection and/or transmission properties of the particles as recorded by said camera system.

24. The apparatus of claim 18 wherein said digital image processing system is adapted to use neural networks in determining said somatic cell or fat droplet count score from said two-dimensional images.

25. The apparatus of claim 18 wherein
said milking of said milking animal is performed by an automated or semi-automated milking system, which comprises a plurality of teat cups, each of which being connected to a respective milk line, which milk lines in turn are connected to a container, wherein, during milking of the teats of said milking animal, said plurality of teat cups are attached to the teats of the milking animal and vacuum is supplied to said container to draw milk through said milk lines and into said container; and
said measuring chamber, through which said at least portion of said milk is flowed, is arranged within one of said milk lines.

26. The apparatus of claim 25 wherein said measuring chamber is defined by a light transparent plate mounted in a wall of said one of said milk lines, through which said two-dimensional camera system is adapted to record said two-dimensional images; and an oppositely located substantially flat and parallel surface.

27. The apparatus of claim 26 wherein said measuring chamber is open in directions being parallel with said light transparent plate and said substantially flat surface, and orthogonal to a general direction of the flow of said at least portion of said milk.

28. The apparatus of claim 26 wherein said substantially flat surface is rotatable around an axis being orthogonal to said light transparent plate and said substantially flat surface.

29. The apparatus of claim 26 wherein said substantially flat surface is an end surface of a rod.

30. The apparatus of claim 29 wherein said rod is light transparent to allow for illumination through said rod of said milk that flows through said measuring chamber.

31. The apparatus of claim 25 wherein said container is provided with a plurality of milk output lines; and said apparatus further comprises a pump and regulator system connected to said digital image processing system for pumping said milk drawn through the milk lines and into said container out through one of said plurality of milk output lines depending on said somatic cell or fat droplet count score.

32. The apparatus of claim 25 wherein
each of said milk lines is provided with a measuring chamber, through which a portion of the milk drawn through the respective milk line is passed;
said light source system is adapted to illuminate milk that flows through each of said measuring chambers;
said two-dimensional camera system is adapted to repeatedly record two-dimensional digital images of illuminated milk that flows through each of said measuring chambers; and
said digital image processing system is adapted to determine a somatic cell or fat droplet count score for milk drawn through each of said milk lines from said two-dimensional images.

33. The apparatus of claim 18 wherein
said milking of said milking animal is performed by an automated or semi-automated milking system, which comprises a plurality of teat cups, each of which being connected to a respective milk line, wherein, during milking of the teats of said milking animal, said plurality of teat cups are attached to the teats of the milking animal and vacuum is supplied to said teat cups through said milk lines to draw milk through said milk lines;
each of said milk lines is provided with a measuring chamber, through which a portion of the milk drawn through the respective milk line is passed;
said light source system is adapted to illuminate milk that flows through each of said measuring chambers;
said two-dimensional camera system is adapted to repeatedly record about 1000 or more two-dimensional digital images of illuminated milk that flows through each of said measuring chambers;
said digital image processing system is adapted to determine a somatic cell or fat droplet count score for milk drawn through each of said milk lines from said two-dimensional images; and
a directing means connected to said digital image processing system for directing milk drawn through each of the respective milk lines into a selected one of a plurality of containers depending on the respective somatic cell or fat droplet count score.

34. The method of claim 1, wherein the magnification lens system is a high-magnification lens system providing a spatial resolution in the digital images of about 0.5 microns or less.

35. The apparatus of claim 18, wherein the magnification lens system is a high-magnification lens system providing a spatial resolution in the digital images of about 0.5 microns or less.

36. The method of claim 1, wherein the somatic cells are distinguished from the fat droplets by analyzing at least one of shape, size, structure, density, and composition in the digital images.

37. The apparatus of claim 18, wherein the digital imaging processing system is configured to distinguish the somatic cells from the fat droplets by analyzing at least one of shape, size, structure, density, and composition in the digital images.

* * * * *